United States Patent [19]
Ryd et al.

[11] Patent Number: 5,087,261
[45] Date of Patent: Feb. 11, 1992

[54] SAW-BLADE FOR SAWING LIVING HUMAN BONE

[75] Inventors: Leif E. S. H. Ryd; Anders O. Bertilsson-Lindstrand, both of Lund; Sören Toksvik-Larsen, Staffanstorp, all of Sweden

[73] Assignee: MIT AB, Sjobo, Sweden

[21] Appl. No.: 572,946

[22] PCT Filed: Mar. 17, 1988

[86] PCT No.: PCT/SE89/00141
§ 371 Date: Sep. 20, 1990
§ 102(e) Date: Sep. 20, 1990

[87] PCT Pub. No.: WO89/09028
PCT Pub. Date: Oct. 5, 1989

[30] Foreign Application Priority Data
Mar. 21, 1988 [SE] Sweden ................................. 8801016

[51] Int. Cl.⁵ ............................................. A61B 17/14
[52] U.S. Cl. ........................................ 606/82; 606/177;
30/123.3; 83/169; 83/171
[58] Field of Search ............... 30/515, 123.3; 606/176,
606/177, 178, 82; 83/169, 171

[56] References Cited
U.S. PATENT DOCUMENTS
4,008,720 2/1977 Brinckmann et al. .

FOREIGN PATENT DOCUMENTS
1565396 5/1969 France .
WO 86/05727 10/1986 PCT Int'l Appl. .

*Primary Examiner*—Michael H. Thaler
*Attorney, Agent, or Firm*—Bacon & Thomas

[57] ABSTRACT

A saw-blade for sawing living human bone during surgical operations, the saw-blade (1) presenting on at least one side (10) at least two saw portions (8, 9) and said saw-blade (1) having at least one inner space (14) through which coolant (18) is adapted to flow for cooling the saw-blade (1) during sawing. For efficient direct cooling of the saw portions (8, 9) and continuous cleaning thereof during sawing, the space (14) extends up to the two saw portion (8, 9) and is open between them in order, on one hand, to conduct coolant (18) to the saw portions (8, 9) for cooling them, and, on the other hand, to cause coolant (18) to emerge between the saw portions (8, 9) for carrying off bone residues or other saw residues in a direction away from the saw portions (8, 9).

10 Claims, 5 Drawing Sheets

SAW-BLADE FOR SAWING LIVING HUMAN BONE

BACKGROUND OF THE INVENTION

This invention relates to a saw-blade for sawing living human bone during surgical operations.

DISCUSSION OF RELATED TECHNOLOGY

Operations in orthopedic surgery often involve shortening, cutting, cleaving or otherwise working bone structures. This is done by chisel, drill, sometimes by milling cutters and sometimes, where straight cuts or planar bone surfaces are desired, by saws. To ensure precision in sawing very high speeds on the order of 20,000 rpm are used, so the saw "vibrates" in a stable manner. This way of working the bone is customary at operations involving artificial joints (joint prostheses), especially in the knee joint. However, also when operations are made in the hip joint and joints in the upper extremity, use is made of sawing.

Artificial joints are fixed to the bone tissue by means of so-called bone cement (acrylic plastic) or by promoting growth of bone directly into the prosthesis. Such anchoring at present is the greatest problem in prosthesis surgery; if the prostheses comes loose from the bone tissue, another operation is required. A corresponding problem exists at operations not involving a prosthesis, i.e. where bone is sawn off and screwed together at another angle. In some cases, the bone does not heal after such operation.

With the use of extant saws, high temperatures develop. By way of example, there have been measured in the clinical situation, at an operation involving an artificial joint in the knee joint, temperatures ranging between 45° and >100° C., the average value being about 70° C. The critical temperature for bone tissue is considered to lie at 47° C. The conclusion is that the bone around the saw cut is killed during the operation. This may be one of the reasons why prostheses come loose and, respectively, that healing sometimes does not occur in the contemplated manner.

During sawing at this kind of operations it is customary to cool the bone by supply of liquid dropwise to the saw-blade or by spraying liquid thereonto. In laboratory tests as well as under clinical conditions, it has proved that such cooling has no effect at all; the problem of heat development on sawing in orthopedics is still unsolved at present.

In patent literature there are some specifications that treat of the supply of coolant to the saw-blade for the cooling thereof. Thus U.S. Pat. No. 4,008,720 describes a saw-blade having three coolant passages. At the rear portions of the saw-blade said passages connect onto a coolant supply conduit and extend in a forward direction along the saw-blade, opening at a distance from the saw teeth in one of the saw-blade sides which run in parallel with the plane of oscillation of the saw-blade. The passages opening at a distance from the saw teeth, the coolant will not contact said teeth, which implies that they are not cooled directly. Instead, the heat has time to spread rearwardly in the saw-blade until it reaches cooled portions thereof, and the harm is done already. Moreover, since the passages open into those sides of the saw-blade which run in parallel with the plane of oscillation of the saw-blade, the exiting coolant jets will not be directed outwardly away from the saw-blade for efficiently carrying off saw residues in a direction away from the saw teeth.

BRIEF SUMMARY OF THE INVENTION

The object of the present invention is to provide a saw-blade in which the above-mentioned problems are eliminated. This is achieved, according to the invention, by using a saw blade presenting on at least one side at least two saw portions and the saw blade having at least one inner space through which coolant is intended to flow for cooling the saw blade during sawing.

As the coolant space in the saw-blade according to the invention extends all the way to the saw portions, coolant can get in direct contact with said portions for efficient direct cooling thereof. Moreover, as coolant can emerge between the saw teeth, the coolant is able to flush away saw residues from the saw teeth, which will prevent clogging of the teeth during sawing.

Practical tests have shown that the temperature of all portions of the saw-blade according to the invention is fully controllable; it has been possible, quite easily, to maintain a saw-blade temperature of maximally 25° C. It has further proved that said coolant effectively flushes the saw teeth and prevents clogging of them, as a result of which it has been possible to increase the sawing effect and, as a consequence, to reduce the time of operation.

DESCRIPTION OF THE DRAWINGS

The invention is more fully elucidated in the following with reference to the accompanying drawings, in which.

DETAILED DESCRIPTION OF PREFERRED EMBODIMENTS

Figure 8:
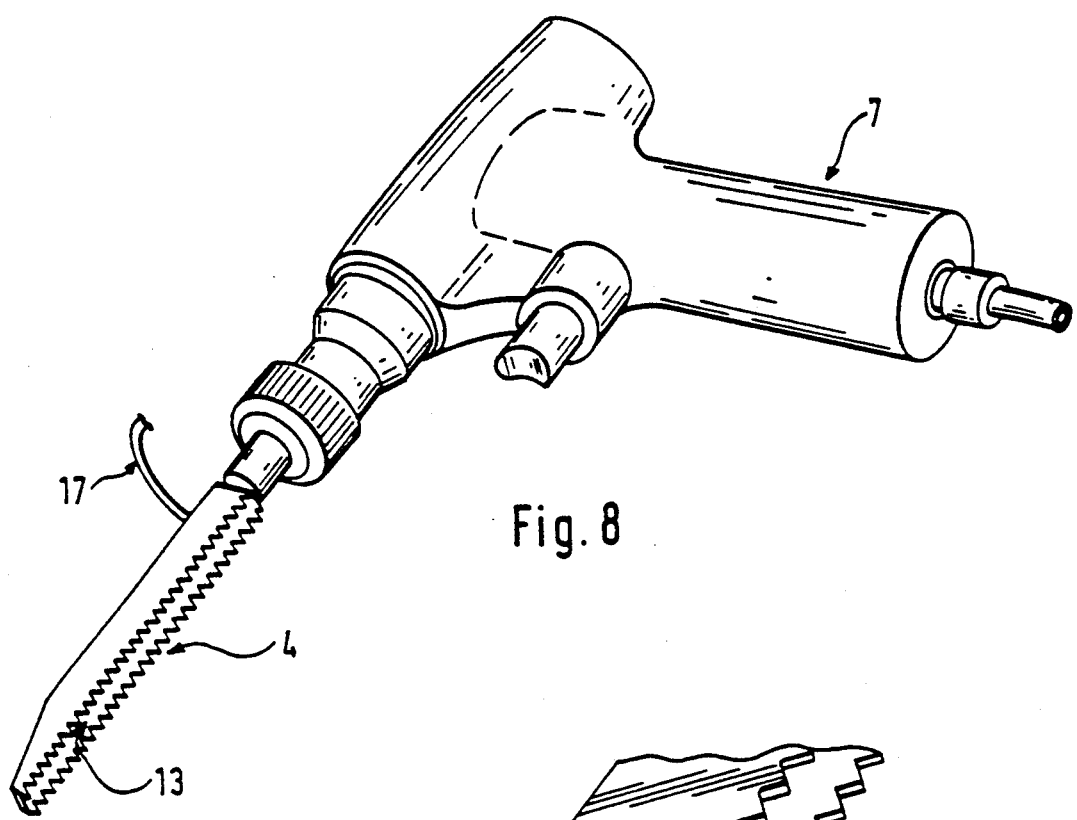
FIG. 8 is a perspective view of a third alternative embodiment of the saw-blade according to the invention.
Figure 9:
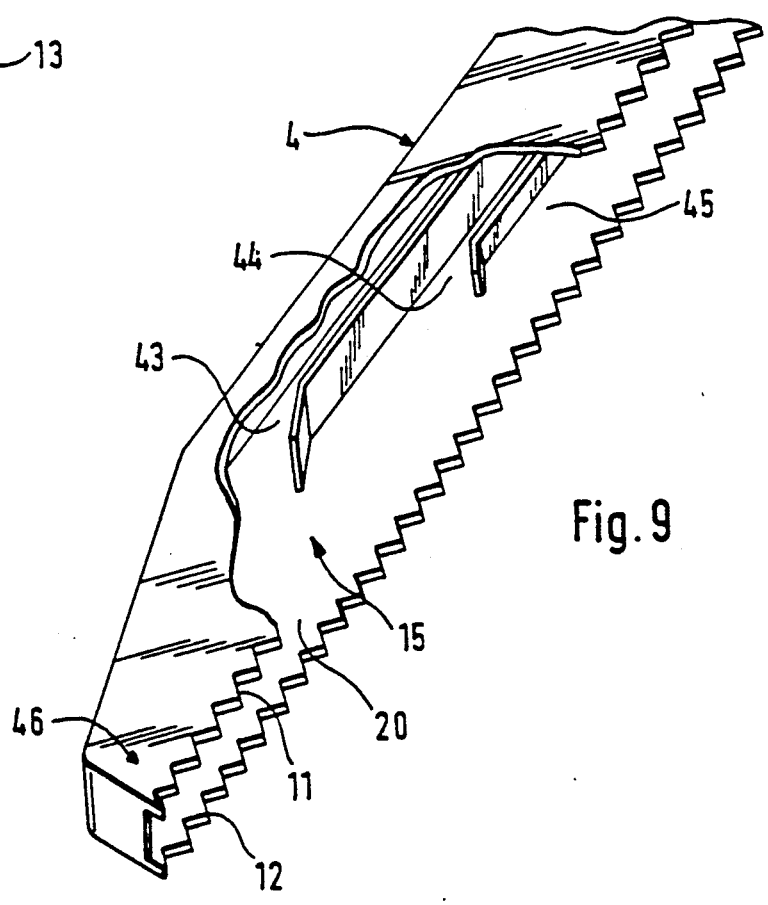
FIG. 9, finally, is a perspective view, partly in section, of the front part of the saw-blade shown in FIG. 8.

The saw-blades 1, 2, 3 and 4 illustrated in the drawing figures are primarily intended for sawing living human bone at operations in orthopedic surgery, but they may also be used in other kinds of surgical operations. The saw-blades 1, 2, 3 according to FIGS. 1 to 6 are attachable to a drive assembly 5 which is adapted to oscillate the saw-blades 1, 2 and 3 back and forth at high speed, e.g. about 20,000 rpm, about a center of oscillation 6. The saw-blade 4 according to FIGS. 8 and 9 is attachable to a drive assembly 7 which is adapted to reciprocate the saw-blade 4 rectilinearly at high speed. The saw-blades 1 to 3 comprise two saw portions 8, 9 on one side 10 of the saw-blade, while the saw-blade 4 comprises two saw portions 11, 12 on one side 13 of the saw-blade. The saw-blades 1 to 3 have an inner space or duct 14 and the saw-blade 4 has a corresponding inner space or duct 15. The space 14 is connected via a conduit 16 to a coolant supply device (not shown) which comprises for instance a coolant container and a pump for providing a certain coolant pressure in the saw-blade. Correspondingly, the space 15 of the saw-blade 4 is connected via a conduit 17 to a coolant supply device (not shown).

The coolant supplied from the respective coolant device 18 preferably is a liquid of suitable type or, alternatively, a gas. The respective coolant supply device suitably delivers a coolant flow of 30 to 90 ml per minute, preferably 70 to 90 ml per minute, at the outlet openings of the respective spaces 14 and 15.

Figure 1:
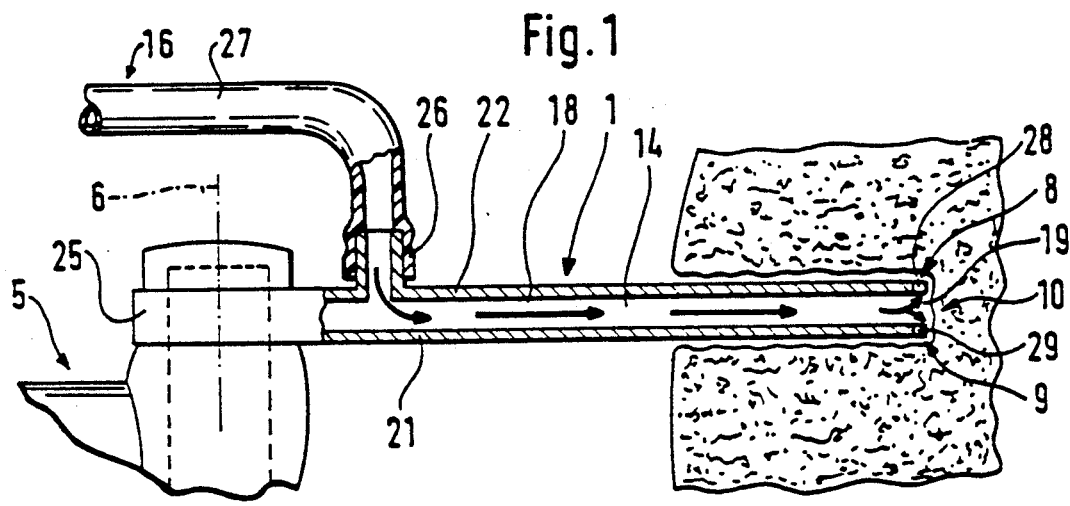
FIG. 1 is a side view, partly in section, of the saw-blade according to the invention.
Figure 2:
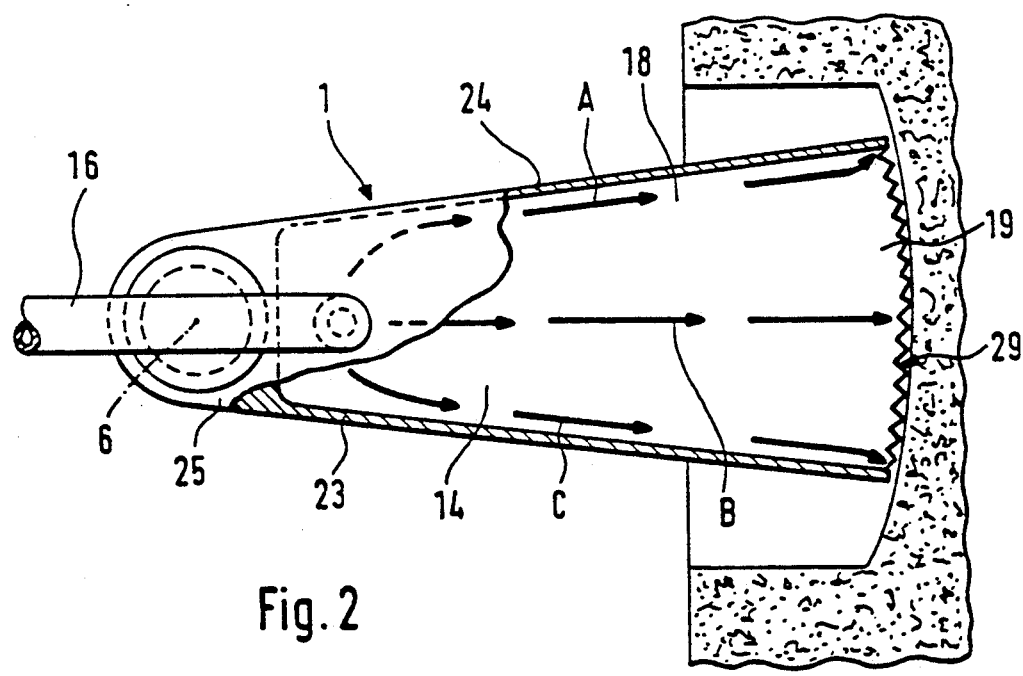
FIG. 2 is a plan view of the saw-blade shown in FIG. 1.
Figure 3:
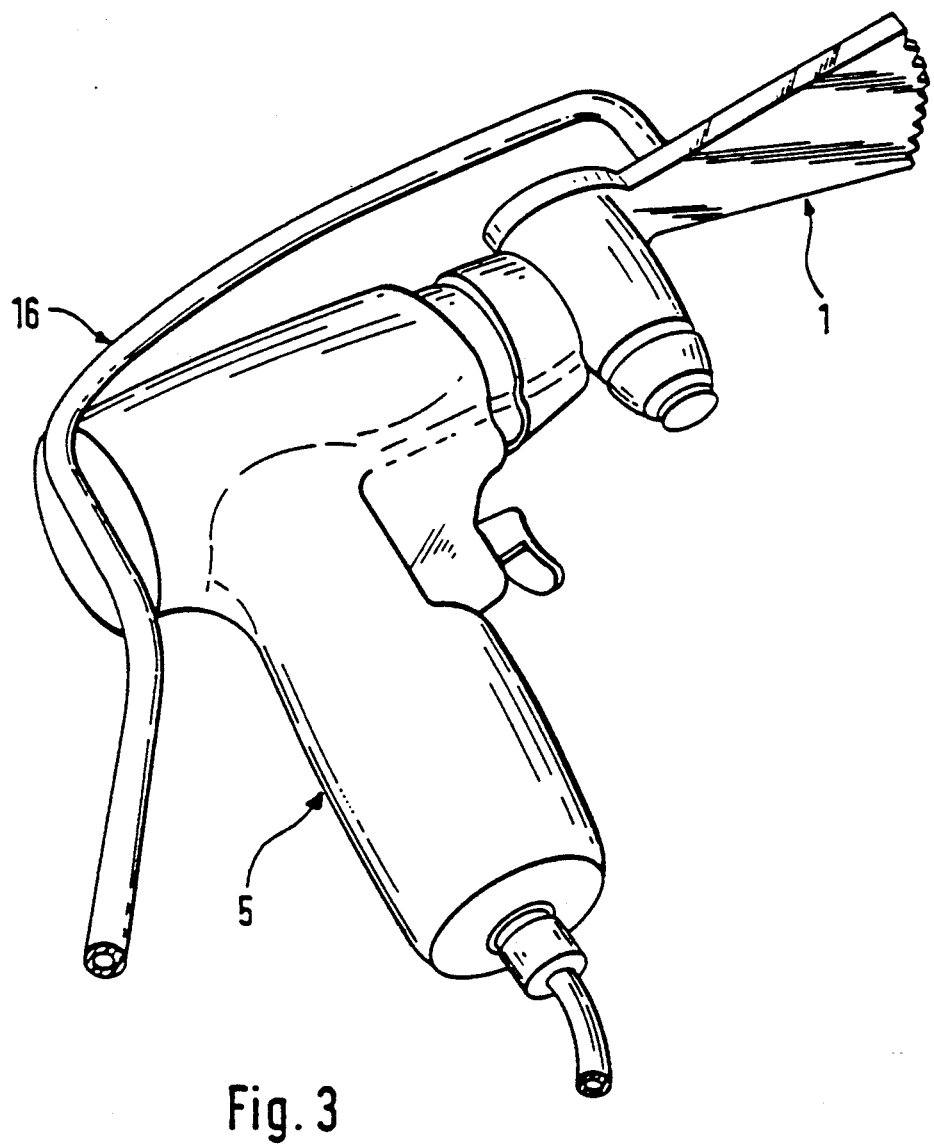
FIG. 3 is a perspective view of the saw-blade according to the invention and the driving tool therefor.
Figure 4:
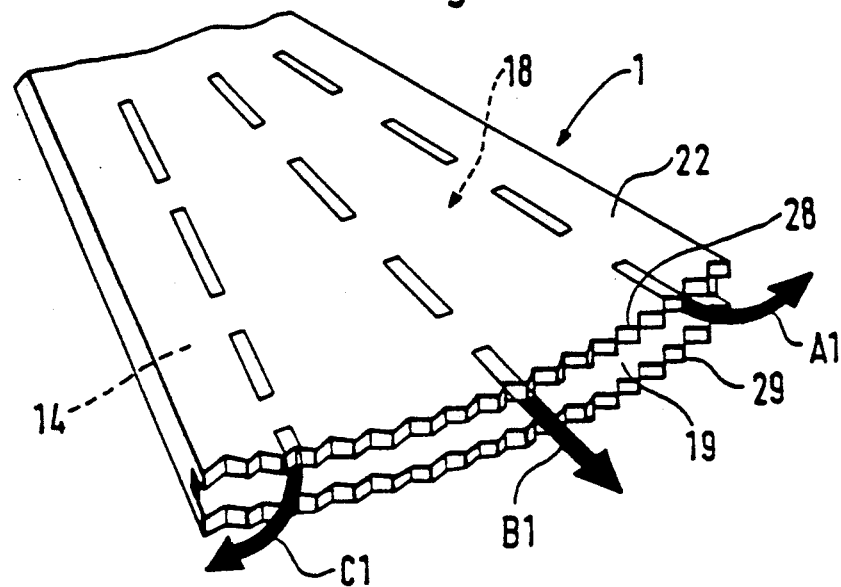
FIG. 4 is a perspective view of a front part of the saw-blade according to the invention.

For efficient cooling of the saw-blade 1, 2, 3 and 4, respectively, the space 14 and 15, respectively, extends up to and terminates at the two saw portions 8, 9 and 11, 12, respectively, and said space is open between said saw portions—via an outlet opening 19 and 20, respectively—on the one hand, to conduct coolant 18 to the saw portions 8, 9 and 11, 12, respectively, (arrow A, B, C; FIG. 2) for the cooling thereof, and on the other hand, to cause coolant 18 to emerge between the saw portions 8, 9 and 11, 12, respectively, (arrow A1, B1, C1; FIG. 4) for carrying off bone residues or other saw residues in a direction away from the saw portions 8, 9 and 11, 12, respectively.

In the embodiment illustrated in FIGS. 1 to 6 the saw-blade 1, 2 and 3, respectively, is in the form of an elongated flattened tube of substantially rectangular cross-sectional shape. Said saw-blade 1, 2 and 3, respectively, has two parallel sides 21 and 22 which are also parallel with the plane of oscillation in which the saw-blade oscillates. The sides 21, 22 are interconnected via substantially narrower sides 23, 24 so as to constitute a rectangular shape of substantially larger width than height.

Said saw-blade 1, 2 and 3, respectively, has a rear fastening portion 25 by which it is connectable to the drive assembly 5. In proximity to the fastening portion 25 there is arranged, on the side 22 parallel with the plane of oscillation, a hose nipple 26 on to which a hose 27 is passed. The hose 27 is part of the conduit 17 for supply of coolant 18 from the coolant supply device to the space 14.

The square tube is open at the front end so as to form the outlet opening 19 between the saw portions 8 and 9 that are formed in that the front end edges of the parallel sides 21, 22 are provided with saw tooth rows 28, 29.

The space 14 intended for coolant 18 preferably widens in the forward direction towards the side 10 thereof having the saw portions 8, 9 and is substantially as wide as said side 10 and opens into the outlet opening 19 which is substantially as wide as said side 10. As a result, coolant 18 can reach the saw portions 8, 9 in their entire widths, being thus capable of cooling all parts thereof. Suitably, the saw portions 8, 9 are also substantially as long as the side 10.

This embodiment of the saw-blade 1 to 3 permits coolant 18 to enter the blade at the rear thereof and to flow forwardly along the inside of all four sides 21 to 24 directly to the saw tooth rows 28 and 29, exiting through the front outlet opening 19 and finally flowing in the forward direction away from the saw tooth rows 28, 29. This implies that coolant 18 cools all sides 21 to 24 of the saw-blade along substantial parts of their lengths; it cools the saw tooth rows 28, 29 by getting in direct contact with them, and when coolant 18 flows out of the outlet opening 19 it carries along bone residues and other saw residues from the saw tooth rows 28, 29, i.e. it cleans said rows simultaneously as coolant 18 continuously counteracts clogging of the saw tooth rows 28, 29.

Figure 5:
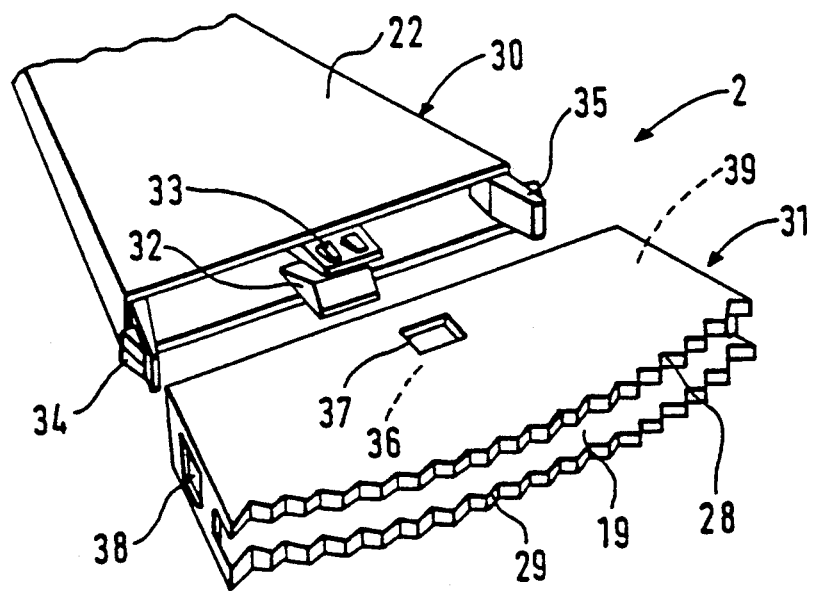
FIG. 5 is a perspective view of an alternative embodiment of the saw-blade according to the invention.

The saw-blade may be a single unit as shown in FIGS. 1 to 4 but, alternatively, it may comprise two separate parts 30, 31 as shown in FIG. 5. This saw-blade 2 thus consists, on one hand, of a fastening member 30 provided with the fastening portion 25 and, on the other hand, of a front member 31 provided with the saw portions 8, 9. These two members 30, 31 are suitably interconnectable and again disconnectable. For instance, the fastening member 30 may comprise four claws 32 to 35 which are arranged each on their respective sides 21 to 24, and the front member 31 comprises recesses 36 to 39 corresponding to the claws 32 to 35.

The claws 32 to 35 are resilient or have resilient studs so that, on one hand, they can yield when the front member 31 is moved towards the fastening member 30, and, on the other hand, snap into the recesses 36 to 39 of the fastening member 31. To disengage the front member 31 from the fastening member 30 the claws 32 to 35 have to be urged out of the recesses 36 to 39 with the aid of a special disengagement tool, whereby it is ensured that the front member 31 cannot come loose or be released involuntarily.

This embodiment of the saw-blade 2 permits using a fastening member 30 over a long period, while a used front member 31 may be exchanged, after say one operation or a few operations, for a new one.

Figure 6:
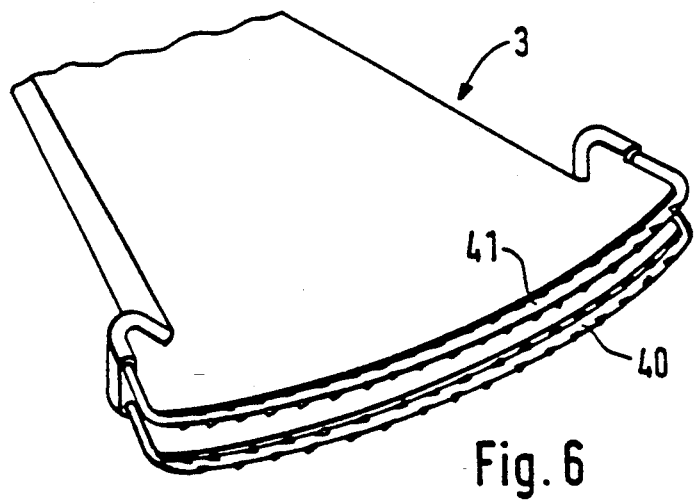
FIG. 6 is a perspective view of a second alternative embodiment of the saw-blade according to the invention.
Figure 7:
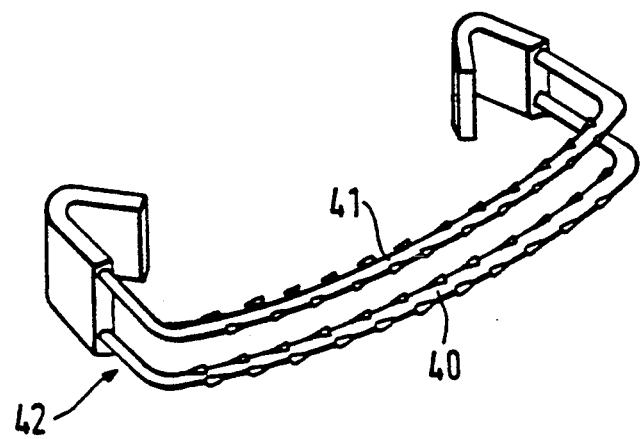
FIG. 7 illustrates a saw wire device for the saw-blade shown in FIG. 6.

A further alternative of the saw-blade is shown in FIG. 6. The saw-blade 3 according to this alternative has saw portions 8, 9 in the form of saw wires 40 and 41. These are preferably detachably mounted on the square tube so as to bear against the front edges of the sides 21, 22. The saw wires 40, 41 are preferably comprised in a unit 42 which is detachably mounted on the square tube to permit being dismounted with the aid of a releasing tool and replaced whenever necessary.

Finally, FIGS. 8 and 9 illustrate a saw-blade 4 in the form of an elongated blade which is disposed on the drive assembly 7. Said assembly is intended to impart linear reciprocating saw movements to the saw-blade 4 and is designed in a manner known per se. The saw-blade 4 has an inner space 15 to which is connected the conduit 17 coming from the coolant supply device. The saw portions 11, 12 of the saw-blade 4 extend along one long side 13 of the blade and said long side is fully open so as to form the outlet opening 20 for coolant between the saw portions 11, 12. The latter need not extend along the entire blade but possibly only along a part thereof, in which case the outlet opening 20 does not either extend along the entire blade but only along a part thereof. The inner space 15 of the blade is preferably divided into longitudinal passages 43 to 45, one of the passages (in the present instance, the passage 43) being adapted to conduct coolant 18 to a front end portion 46 of the saw-blade 4. It is thereby ensured that coolant 18 reaches the front end portions of the saw-blade 4, which is important because the saw portions 11, 12 at this end portion will be warmest and thus need be effectively cooled.

The coolant supply device is preferably adapted to supply coolant in the form of a cooling liquid to the space 14 and 15, respectively, at such a pressure that the coolant delivery in the outlet opening 19 and 20, respectively, amounts to 30 to 90 ml per minute, preferably 70 to 90 ml per minute. Such a coolant flow has proved to produce a particularly favorable cooling effect and a good saw portion cleaning effect without any negative effects, for instance in the form of splashing.

The embodiments of the saw-blade described above and illustrated in the drawings may be varied within the scope of the appendant claims, with regard to design and function. As examples of further embodiments, it should be mentioned that the saw tooth rows 28, 29 or the saw tooth wires 40, 41 may be arcuate, extending along arcs the centers of which are centered with the center of oscillation 6 of the saw-blade 1, 2 and 3, respectively. The saw-blade may possibly have saw portions on more than one side and at more than two edges. There may also be more than one outlet opening for coolant and the inner space may be divided into a number of separate sections, maintaining however the extension of the space up to the side provided with the saw portions. Any suitable liquid may serve as coolant, but it may be possible to use gas instead of liquid.

We claim:

1. A saw blade for sawing living human bone during surgical operations, said saw blade comprising an elongated flattened tube having a substantially rectangular cross section and terminal edges including at least a pair of spaced parallel edges extending along one side of the saw blade, said tube defining a coolant duct terminating at and between said terminal edges over substantially the full length of the terminal edges; saw portions disposed along at least said pair of spaced parallel terminal edges with the terminus of said duct disposed between the saw portions; and means for admitting coolant to the duct; whereby coolant may be circulated throughout the duct and between the saw portions.

2. A saw blade as claimed in claim 1 including a drive assembly means for imparting to the saw blade reciprocating oscillation movements in an oscillation plane, and wherein the saw blade has a rear fastening portion for the mounting of the saw blade to the drive assembly means, said means for admitting coolant to the duct disposed in close proximity to the fastening portion.

3. A saw blade as claimed in claim 2 wherein the saw blade includes a flat side extending parallel to said oscillation plane, and wherein said means for admitting coolant to the duct is disposed on said flat side.

4. A saw blade as claimed in claim 1, wherein the tube comprises two separate parts including a fastening member having a fastening portion for the mounting thereof on a drive assembly, and a front member provided with the saw portions, said tube members being interconnectable and again disconnectable after use.

5. A saw blade as claimed in claim 4, wherein the fastening member and the front member are provided with coupling means for permitting the members to be engaged by snap action and also for permitting the members to be disengaged after use from one another.

6. A saw blade as claimed in claim 1, wherein the coolant duct widens from a side of the saw blade opposite the saw portions towards the side thereof provided with the saw portions.

7. A saw blade as claimed in claim 1, wherein the saw portions of the saw blade comprise two saw wires, and means to disengaging the saw wires from the saw blade to permit exchange of said wires after use.

8. A saw blade as claimed in claim 1, wherein said pair of spaced parallel edges extend along a long side of the saw blade, and wherein the saw portions of the saw blade are arranged along said long side of the saw blade, said saw blade including a front end portion, said duct terminating at said long side and including longitudinal passages for conducting coolant to said front end portion.

9. A saw blade as claimed in claim 1, wherein the means for admitting coolant to the duct is connected to a coolant supply device which provides a coolant flow of 30-90 ml per minute at the terminus of the duct.

10. A saw blade as claimed in claim 9, wherein the means for admitting coolant to the duct is connected to a coolant supply device which provides a coolant flow of 70-90 ml per minute at the terminus of the duct.

* * * * *